(12) United States Patent
Bowe (10) Patent No.: US 6,592,581 B2
(45) Date of Patent: *Jul. 15, 2003

(54) PREFORMED STEERABLE CATHETER WITH MOVABLE OUTER SLEEVE AND METHOD FOR USE

(75) Inventor: Wade A. Bowe, Temecula, CA (US)

(73) Assignee: Cardiac Pacemakers, Inc., St. Paul, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 99 days.

(21) Appl. No.: 09/746,721

(22) Filed: Dec. 22, 2000

(65) Prior Publication Data

US 2001/0039413 A1 Nov. 8, 2001

Related U.S. Application Data

(60) Continuation-in-part of application No. 09/516,280, filed on Mar. 1, 2000, now Pat. No. 6,270,496, which is a division of application No. 09/072,962, filed on May 5, 1998, now Pat. No. 6,096,036.

(51) Int. Cl.[7] ............................................. A61B 18/18
(52) U.S. Cl. ........................ 606/41; 604/530; 600/585; 607/122
(58) Field of Search ................................ 604/530, 264, 604/531, 532, 523, 528; 606/41; 600/585, 372, 374; 607/122

(56) References Cited

U.S. PATENT DOCUMENTS

| 4,917,102 A | 4/1990 | Miller et al. ............... 128/772 |
| 4,960,134 A | 10/1990 | Webster, Jr. ............... 128/786 |
| 5,171,232 A | 12/1992 | Castillo et al. ............. 604/280 |
| 5,363,861 A | * 11/1994 | Edwards et al. ............ 128/772 |
| 5,383,923 A | 1/1995 | Webster, Jr. ................ 607/125 |
| 5,476,495 A | 12/1995 | Kordis et al. ............... 607/122 |
| 5,487,385 A | 1/1996 | Avitall ....................... 128/642 |
| 5,487,757 A | 1/1996 | Truckai et al. .............. 128/642 |
| 5,489,270 A | 2/1996 | van Erp ....................... 604/95 |
| 5,500,012 A | 3/1996 | Brucker et al. |
| 5,531,685 A | 7/1996 | Hemmer et al. ............... 604/95 |
| 5,582,609 A | 12/1996 | Swanson et al. .............. 604/39 |

(List continued on next page.)

FOREIGN PATENT DOCUMENTS

| EP | 790066 A2 | 2/1992 | |
| EP | 0745406 A2 | 12/1996 | .......... A61M/25/00 |
| EP | 778043 A1 | 12/1996 | |
| WO | WO94/21168 | 9/1994 | |
| WO | WO926836 | 7/1997 | |

*Primary Examiner*—Linda C. M. Dvorak
*Assistant Examiner*—David M. Ruddy
(74) *Attorney, Agent, or Firm*—Fulwider Patton Lee & Utecht, LLP (57) ABSTRACT

A wire housed within a sheath is formed of a shape-retentive and resilient material having a curved shape at its distal-end region resulting in the catheter sheath having the curved shape. The catheter sheath also has an axially oriented tendon for causing deflection of the distal-end region. A movable outer sleeve surrounds the sheath and conforms the portion of the wire positioned within the outer sleeve to the shape of the outer sleeve. Upon relative displacement of the sheath and the outer sleeve a portion of the sheath extends beyond the outer sleeve and resumes its preformed curved distal shape thereby forcing the catheter distal-end region into the same curved shape. The operator may adjust the relative positions of the sheath and outer sleeve to changes the shape of the distal-end region. The operator may also axially move the tendon to adjust the radius or curvature of the distal-end region.

21 Claims, 7 Drawing Sheets

U.S. PATENT DOCUMENTS

| | | | |
|---|---|---|---|
| 5,617,854 A | | 4/1997 | Munsif ........................ 128/642 |
| 5,626,136 A | * | 5/1997 | Webster, Jr. ................. 128/642 |
| 5,637,090 A | | 6/1997 | McGee et al. ................. 604/95 |
| 5,715,817 A | | 2/1998 | Stevens-Wright et al. .. 128/642 |
| 5,797,842 A | | 8/1998 | Pumares et al. |
| 5,823,955 A | * | 10/1998 | Kuck et al. .................. 600/374 |
| 5,842,984 A | | 12/1998 | Avitall |
| 5,860,920 A | * | 1/1999 | McGee et al. ............... 600/374 |
| 5,882,346 A | * | 3/1999 | Pomeranz et al. ........... 607/122 |
| 6,200,315 B1 | | 3/2001 | Gaiser |
| 6,402,746 B1 | * | 6/2002 | Whayne et al. ................ 606/41 |

* cited by examiner

PREFORMED STEERABLE CATHETER WITH MOVABLE OUTER SLEEVE AND METHOD FOR USE

RELATED APPLICATIONS

This is a continuation-in-part of application Ser. No. 09/516,280, filed Mar. 1, 2000, now U.S. Pat. No. 6,270,496, which is a division of application Ser. No. 09/072,962, filed May 5, 1998, now U.S. Pat. No. 6,096,036.

BACKGROUND OF THE INVENTION

The invention relates generally to an electrophysiological ("EP") apparatus and method for providing energy to biological tissue, and more particularly, to a steerable catheter with a preformed distal shape and a movable outer sleeve for positioning the catheter to a desired location in a patient.

The heart beat in a healthy human is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth of, or damage to, the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as "cardiac arrhythmia."

While there are different treatments for cardiac arrhythmia, including the application of anti-arrhythmia drugs, in many cases ablation of the damaged tissue can restore the correct operation of the heart. Such ablation can be performed by percutaneous ablation, a procedure in which a catheter is percutaneously introduced into the patient and directed through an artery or vein to the atrium or ventricle of the heart to perform single or multiple diagnostic, therapeutic, and/or surgical procedures. In such case, an ablation procedure is used to destroy the tissue causing the arrhythmia in an attempt to remove the electrical signal irregularities or create a conductive tissue block to restore normal heart beat or at least an improved heart beat. Successful ablation of the conductive tissue at the arrhythmia initiation site usually terminates the arrhythmia or at least moderates the heart rhythm to acceptable levels. A widely accepted treatment for arrhythmia involves the application of RF energy to the conductive tissue.

In the case of a trial fibrillation ("AF"), a procedure published by Cox et al. and known as the "Maze procedure" involves continuous atrial incisions to prevent atrial reentry and to allow sinus impulses to activate the entire myocardium. While this procedure has been found to be successful, it involves an intensely invasive approach. It is more desirable to accomplish the same result as the Maze procedure by use of a less invasive approach, such as through the use of an appropriate EP catheter system.

There are two general methods of applying RF energy to cardiac tissue, unipolar and bipolar. In the unipolar method a large surface area electrode; e.g., a backplate, is placed on the chest, back or other external location of the patient to serve as a return. The backplate completes an electrical circuit with one or more electrodes that are introduced into the heart, usually via a catheter, and placed in intimate contact with the aberrant conductive tissue. In the bipolar method, electrodes introduced into the heart have different potentials and complete an electrical circuit between themselves. In the bipolar method, the flux traveling between the two electrodes of the catheter enters the tissue to cause ablation.

During ablation, the electrodes are placed in intimate contact with the target endocardial tissue. RF energy is applied to the electrodes to raise the temperature of the target tissue to a non-viable state. In general, the temperature boundary between viable and non-viable tissue is approximately 48° Centigrade. Tissue heated to a temperature above 48° C. becomes non-viable and defines the ablation volume. The objective is to elevate the tissue temperature, which is generally at 37° C., fairly uniformly to an ablation temperature above 48° C., while keeping both the temperature at the tissue surface and the temperature of the electrode below 100° C.

Failure to bring or maintain the electrodes in contact with the target tissue may result in the RF energy not reaching the tissue in sufficient quantities to effect ablation. Only limited electromagnetic flux in a bipolar approach may reach the tissue when the electrode is non-contacting. In a unipolar approach, the RF energy may spread out too much from the non-contacting electrode before reaching the tissue so that a larger surface area is impacted by the flux resulting in each unit volume of tissue receiving that much less energy. In both cases, the process of raising the tissue temperature to the ablation point may require a much greater time period, if it can be performed at all. Where the electrodes have temperature sensors and those sensors are not in contact with the tissue, they may not sense the actual temperature of the tissue as fluids flowing around the non-contacting electrode may lower the temperature of the electrode and the temperature sensed by the sensors.

In the treatment of atrial fibrillation, a plurality of spaced apart electrodes are located at the distal end of a catheter in a linear array. RF energy is applied to the electrodes to produce a long linear lesion. With such a linear array, intimate contact between each electrode and the target endocardial tissue is more difficult to maintain in the heart due to the irregular heart surface contours and the constant movement of the heart. The lesion produced may have discontinuities unless steps are taken to maintain contact. These lesions may not be sufficient to stop the irregular signal pathways and arrhythmia may reoccur. Thus the need for catheters having the capability to conform to and maintain intimate contact with various endocardial tissue surface contours is strongly felt by those engaged in the treatment of cardiac arrhythmias, particularly atrial fibrillation.

To that end, several catheter systems have been developed in an attempt to ensure intimate contact between the electrodes at the distal end of a catheter and the target tissue. In one such catheter system, described in U.S. Pat. No. 5,617,854 to Munsif, the distal end of the catheter is shaped to conform to a specific region of the heart. The catheter is made of a shaped-memory material, e.g. nitinol, and formed in a specific shape. During use, the catheter is deformed and introduced through an introducer sheath to the heart where ablation is to occur. Once in position, the sheath is retracted and the catheter is reformed into its specific shape when heated to body temperature or when a current is passed through the shaped-memory material. If the shaped memory of the catheter matches the curvature of the biological cavity, there is more intimate contact between the electrode and the tissue and a more continuous lesion is formed. If a given shaped catheter does not conform to the shape of the biological site to be ablated a different catheter having a different preformed shape must be used. Requiring a collection of preformed-shaped catheters, as such, is economically inefficient.

In another catheter system, described in U.S. Pat. No. 5,882,346, to Pomeranz et al., the catheter system includes a catheter having a lumen extending through it and a plurality of electrodes at the distal-end region. A core wire is insertable into the catheter lumen. The core wire includes a preshaped region that is formed of a superelastic material and which is bent into a predetermined shape. As the core wire is inserted into the catheter, the core wire deforms the distal-end region of the catheter into the predetermined shape of the core wire. If the predetermined shape of the core wire matches the curvature of the biological cavity, there is more intimate contact between the electrodes and the tissue. If, however, a given preshaped core wire does not conform to the shape of the biological site to be ablated a different core wire having a different preformed shape must be used. Thus a collection of different shaped core wires is required. This is also economically inefficient.

Hence, those skilled in the art have recognized a need for providing a single catheter carrying a plurality of electrodes in its distal-end region which is capable of conforming to various curvatures of the biological site so that intimate contact may be maintained between the electrodes and the site. The invention fulfills these needs and others.

SUMMARY OF THE INVENTION

Briefly, and in general terms, the invention is related to an apparatus and a method for use in applying energy to a biological site using a catheter carrying at least one electrode in its distal-end region which is capable of conforming to various curvatures of the biological site so that intimate contact may be maintained between the electrodes and the site.

In a first aspect, the invention is related to a catheter including a sheath having a distal-end region and a wire disposed within the sheath and attached to the distal end of the sheath. The wire has a distal-end region having a preformed shape with a radius of curvature. The wire is formed of a shape-retentive and resilient material such that the wire distal-end region changes shape upon the application of force and upon the removal of force, returns to the preformed shape. The wire is disposed in the sheath such that the wire distal-end region is located in the sheath distal-end and causes the sheath to assume the preformed shape. The catheter further includes an outer sleeve having a distal-end region having a distal end. The sleeve surrounds the sheath and is positioned relative thereto for movement between a retracted position and any of a plurality of advanced positions during which a portion of the sleeve distal-end region is coincident with a portion of the wire distal-end region. The sleeve is formed of a material having a stiffness sufficient to change the shape of the wire distal-end region. The catheter also includes a tendon housed within the sheath. The tendon is attached to the distal end of the sheath such that axial displacement of the tendon changes the radius of curvature of the portion of the wire distal-end region extending distal the distal end of the outer sleeve.

By providing a catheter having a preshaped steerable catheter sheath and a movable outer sleeve surrounding the sheath and having a stiffness sufficient to change the shape of the sheath, the present invention allows for multifaceted adjustment of the distal-end region shape such that intimate contact between the at least one electrode and the target tissue may be obtained regardless of the curvature of the biological site. For example, the preformed shape of distal-end region may be adjusted using the tendon or the movable outer sleeve or a combination of both.

In a more detailed facet of the invention, the outer sleeve has a fully advanced position during which the sleeve distal end is substantially coincident with the wire distal end. In another detailed facet, the outer sleeve has a fully retracted position during which the sleeve distal-end region is proximal the wire distal-end region. In yet another detailed aspect, the outer sleeve distal-end region comprises a preformed shape with a radius of curvature. In still another detailed aspect, the sheath has an axis and the outer sleeve is positioned for rotational movement about the axis of the sheath. In further detailed facets the catheter further includes a locking mechanism for locking the outer sleeve in a position relative to the sheath and a handle having the proximal end of the sheath and the wire connected thereto such that movement of the handle results in movement of the sheath, wire and outer sleeve. In a still another detailed aspect, the tendon is disposed in the sheath such that pulling the tendon in the proximal direction decreases the radius of curvature of the wire distal-end region distal the distal end of the sleeve and subsequent movement of the tendon in the distal direction allows an increase in the radius of curvature of the wire distal-end region distal the distal end of the sleeve.

In a second aspect, the invention is related to an ablation catheter for use in applying energy to heart tissue. The system includes a catheter sheath having a distal-end region, at least one electrode located at the sheath distal-end region and a wire disposed within the sheath and attached to the distal end of the catheter sheath. The wire has a distal-end region with a preformed shape with a radius of curvature and is formed of a shape-retentive and resilient material such that the wire distal-end region changes shape upon the application of force and upon the removal of the force, returns to the preformed shape. The wire is disposed in the catheter sheath such that the wire distal-end region is located in the distal-end region of the sheath and causes the sheath to assume the preformed shape.

The ablation catheter further includes an outer sleeve having a distal-end region having a distal end. The sleeve surrounds the sheath and is positioned relative thereto for movement between a retracted position and any of a plurality of advanced positions during which a portion of the sleeve distal-end region is coincident with a portion of the wire distal-end region. The sleeve is formed of a material having a stiffness sufficient to change the shape of the wire distal-end region. The system also includes a tendon housed within the sheath. The tendon is attached to the distal end of the sheath such that axial displacement of the tendon changes the radius of curvature of the portion of the wire distal-end region extending distal the distal end of the outer sleeve. The system further includes a locking mechanism for locking the outer sleeve in a position relative to the sheath and a handle attached to the proximal end of the catheter sheath and the wire such that movement of the handle causes movement of the catheter sheath, the wire and the outer sleeve.

In a third aspect, the invention involves a method for applying energy to biological tissue within a biological chamber of a patient. The method uses a catheter having a sheath having a distal end-region carrying a plurality of electrodes and a wire disposed within the sheath and attached to the distal end of the sheath. The wire has a distal-end region having a preformed shape with a radius of curvature and is formed of a shape-retentive and resilient material such that the wire distal-end region changes shape upon the application of force and upon the removal of force, returns to the preformed shape. The wire is disposed in the sheath such that the wire distal-end region is located in the sheath distal-end and causes the sheath to assume the preformed shape. The catheter also includes an outer sleeve having a distal-end region having a distal end. The sleeve surrounds the sheath and is positioned relative thereto for movement between a retracted position and any of a plurality of advanced positions during which a portion of the sleeve distal-end region is coincident with a portion of the wire distal-end region. The sleeve is formed of a material having a stiffness sufficient to change the shape of the wire distal-end region. The catheter also includes a tendon housed within the sheath and attached to the distal end of the sheath such that axial displacement of the tendon changes the radius of curvature of the portion of the wire distal-end region extending distal the distal end of the outer sleeve.

The method of the present invention includes the steps of placing the outer sleeve in an advanced position such that the distal end of the sheath is positioned within the outer sleeve, inserting the catheter into the vasculature of the patient and advancing the catheter into the biological chamber in which the selected tissue is located. The method also includes the steps of retracting the outer sleeve such that a portion of the distal-end region of the sheath is positioned outside of the outer sleeve thereby permitting the wire distal-end region to assume the preformed shape and advancing the distal-end region of the catheter sheath to a position proximal the selected biological tissue. The method further includes the step of adjusting the radius of curvature of the distal-end region of the wire to thereby affect adjustment in the distal-end region of the sheath such that a plurality of the electrodes contact the selected biological tissue.

In a detailed facet of the invention, the step of advancing the distal-end region of the catheter sheath to a position proximal the selected heart tissue includes the step of securing the outer sleeve to the sheath and axially displacing the catheter toward the selected biological tissue. In another detailed aspect, the step of advancing the distal-end region of the catheter sheath to a position proximal the selected heart tissue includes the step of maintaining the position of the outer sleeve while axially displacing the catheter sheath toward the selected biological tissue. In yet another detailed facet, the step of adjusting the radius of curvature of the distal-end region of the catheter includes the step of displacing the tendon to deflect the wire distal-end region and thereby decrease the curvature of the wire distal-end region.

These and other aspects and advantages of the invention will become apparent from the following detailed description and the accompanying drawings, which illustrate by way of example the features of the invention.

DETAILED DESCRIPTION OF PREFERRED EMBODIMENTS

Figure 1:
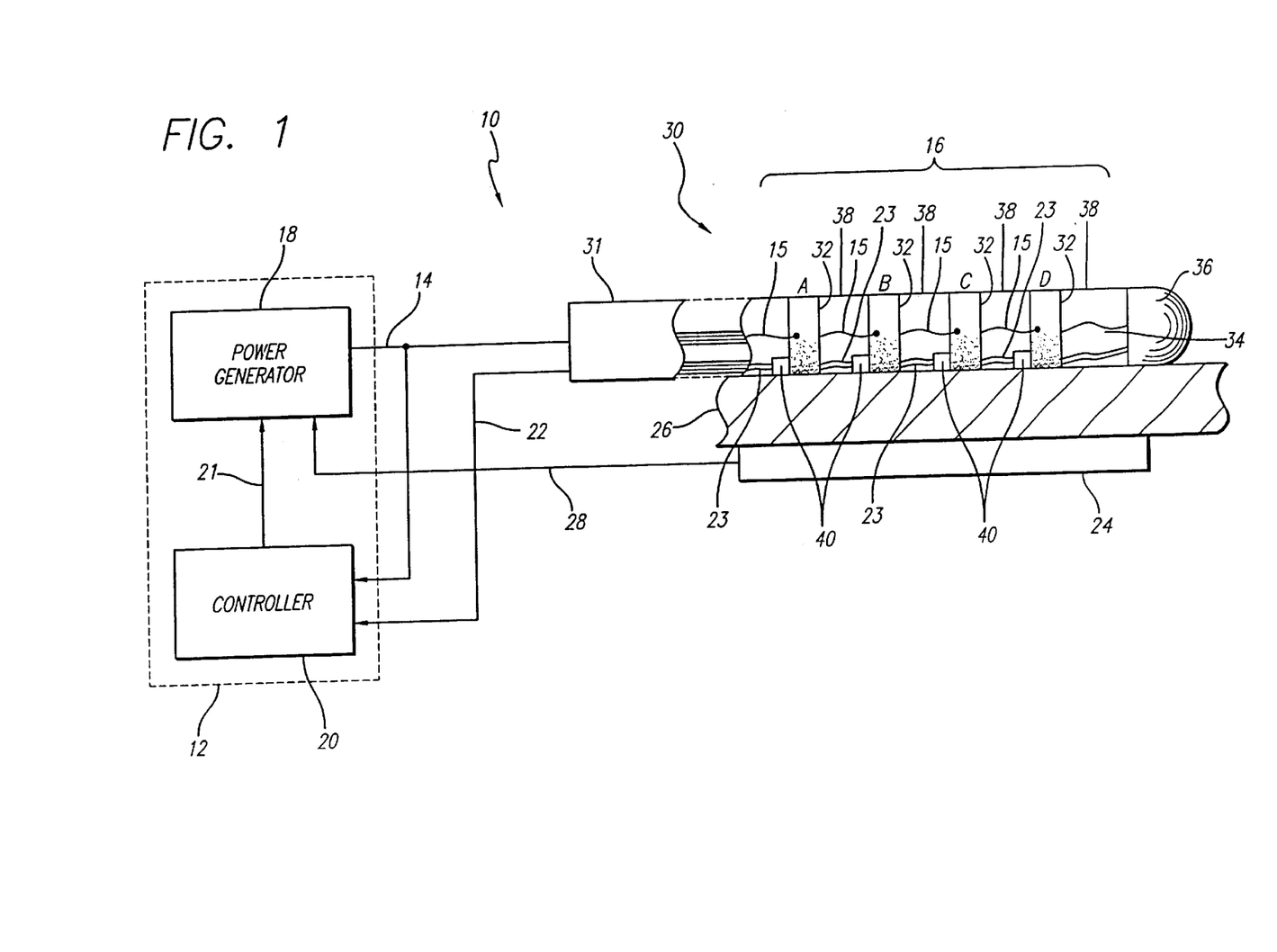
FIG. 1 is a schematic diagram of an ablation apparatus including a power control system, electrode device and backplate.

Turning now to the drawings, in which like reference numerals are used to designate like or corresponding elements among the several figures, in FIG. 1 there is shown an ablation apparatus 10 in accordance with aspects of the present invention. The apparatus 10 includes a power control system 12 that provides power or drive 14 to an electrode device 16. The power control system 12 comprises a power generator 18 that may have any number of output channels through which it provides the power 14. The operation of the power generator 18 is controlled by a controller 20 which outputs control signals 21 to the power generator 18. The controller 20 monitors 15 the power 14 provided by the power generator 18. In addition, the controller 20 also receives temperature signals 22 from the electrode device 16. Based on the power 14 and temperature signals 22 the controller 20 adjusts the operation of the power generator 18. A backplate 24 is located proximal to the biological site 26 opposite the site from the electrode device 16, and is connected by a backplate wire 28 to the power generator 18. The backplate 24 is set at the reference level to the power provided to the electrodes, as discussed in detail below.

In a manual arrangement, the temperature sensed and/or the determined impedance may be displayed to an operator. The operator in response may then manually control the duty cycle or other power parameters using controls, e.g, rotatable knobs, pushbuttons or switches, located on a front panel of an instrument. In the case of a multiple channel instrument and catheter, as discussed below, multiple controls may be provided in this manual arrangement for control over each channel.

The electrode device 16 is typically part of a steerable EP catheter 30 capable of being percutaneously introduced into a biological site 26, e. g., the atrium or ventricle of the heart. The electrode device 16 is shown in schematic form with the components drawn to more clearly illustrate the relationship between the components and the relationship between the components and the power control system 12. In this embodiment, the catheter 30 comprises a distal segment 34 and a handle 31 located outside the patient. A preferred embodiment of the electrode device 16 includes twelve band electrodes 32 arranged in a substantially linear array along the distal segment 34 of the catheter 30. The electrode device 16 may include a tip electrode 36. (For clarity of illustration, only four band electrodes 32 are shown in the figures although as stated, a preferred embodiment may include many more.) The band electrodes 32 are arranged so that there is space 38 between adjacent electrodes. In one configuration of the electrode device 16, the width of the band electrodes 32 is 3 mm and the space 38 between the electrodes is 4 mm. The total length of the electrode device 16, as such, is approximately 8 cm.

The arrangement of the band electrodes 32 is not limited to a linear array and may take the form of other patterns, such as a circular shape for use in ablation therapy around the pulmonary veins. A substantially linear array is preferred for certain therapeutic procedures, such as treatment of atrial fibrillation, in which linear lesions of typically 4 to 8 cm in length are desired. A linear array is more easily carried by the catheter 30 and also lessens the size of the catheter.

The band electrodes 32 are formed of a material having a significantly higher thermal conductivity than that of the biological tissue 26. Possible materials include silver, copper, gold, chromium, aluminum, molybdenum, tungsten, nickel, platinum, and platinum/10% iridium. Because of the difference in thermal conductivity between the electrodes 32 and the tissue 26, the electrodes 32 cool off more rapidly in the flowing fluids at the biological site. The power supplied to the electrodes 32 may be adjusted during ablation to allow for the cooling of the electrodes while at the same time allowing for the temperature of the tissue to build up so that ablation results. The electrodes 32 are sized so that the surface area available for contact with fluid in the heart, e. g., blood, is sufficient to allow for efficient heat dissipation from the electrodes to the surrounding blood. In a preferred embodiment, the electrodes 32 are 7 French (2.3 mm in diameter) with a length of 3 mm.

The thickness of the band electrodes 32 also affects the ability of the electrode to draw thermal energy away from the tissue it contacts. In the present embodiment, the electrodes 32 are kept substantially thin so that the electrodes effectively draw energy away from the tissue without having to unduly increase the outer diameter of the electrode. In a preferred embodiment of the invention, the thickness of the band electrodes is 0.05 to 0.13 mm (0.002 to 0.005 inches).

Associated with the electrode device 16 are temperature sensors 40 for monitoring the temperature of the electrode device 16 at various points along its length. In one embodiment, each band electrode 32 has a temperature sensor 40 mounted to it. Each temperature sensor 40 provides a temperature signal 22 to the controller 20 which is indicative of the temperature of the respective band electrode 32 at that sensor. In another embodiment of the electrode device 16 a temperature sensor 40 is mounted on every other band electrode 32. Thus for a catheter having twelve electrodes, there are temperature sensors on six electrodes. In yet another embodiment of the electrode device 16 every other electrode has two temperature sensors 40. In FIG. 1, which shows an embodiment having one temperature sensor for each electrode, there is shown a single power lead 15 for each electrode 32 to provide power to each electrode for ablation purposes and two temperature leads 23 for each temperature sensor 40.

Figure 2:
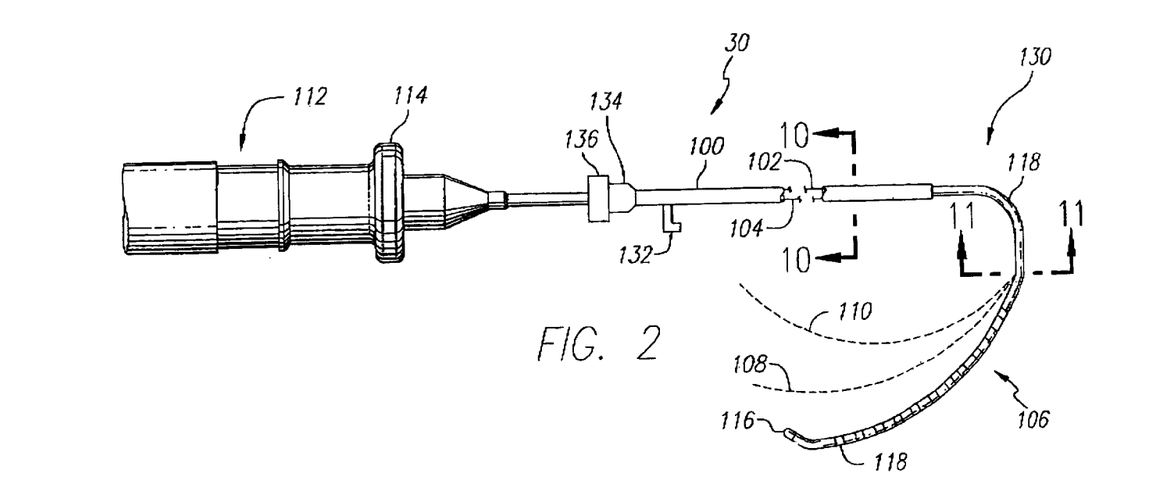
FIG. 2 is a diagram of a catheter system including a handle, steering member, a substantially linear outer sleeve with a locking mechanism, and a catheter sheath having a preformed distal-end region, with the outer sleeve in a retracted position.

With reference to FIG. 2, the catheter 30 includes a sheath 118 having a distal-end region 106 for carrying an electrode device 16 (FIG. 1). The catheter 30 employs a shaped-memory wire, i. e., stylet 104, having a preformed distal shape. The stylet is housed within the sheath 118 such that its preformed distal shape is substantially coincident with the distal-end region 106 and thereby imparts a preformed distal shape to the distal-end region 106. The preformed distal shape may have any form which generally conforms to the contour of the biological cavity containing the tissue to be ablated. In order to ensure more precise placement of the electrode device within a biological site and intimate contact between the electrode device and the biological site, the catheter 30 further employs a steering tendon 102 and outer sleeve 100, which may be used individually or collectively to provide enhanced manipulation of the distal-end region 106.

The distal-end region 106 depicted in FIG. 2 has been simplified for clarity to depict varying degrees of curvature 108, 110 obtainable by use of the preformed shape and the steering tendon, as explained below. The distal shape of FIG. 2 is conducive to the treatment of atrial fibrillation in that its shape allows for the distal-end region 106 to be easily inserted into the atrium of the heart. The shape, in combination with a steering tendon 102, also provides a distal-end region 106 having a contour which may be adjusted to conform to the contour of the atrium.

As previously mentioned, the catheter 30 also includes an outer sleeve 100 that surrounds the sheath 118. The outer sleeve 100 is positioned on the sheath 118 for movement along the length of the sheath and for rotation about the longitudinal axis of the sheath. The outer sleeve 100 includes a handle 134 located at its proximal end for facilitating movement of the sleeve. The sleeve 100 is moveable between a fully retracted position, as shown in FIG. 2, and various advanced positions, one of which is shown in FIG. 3.

Figure 4:
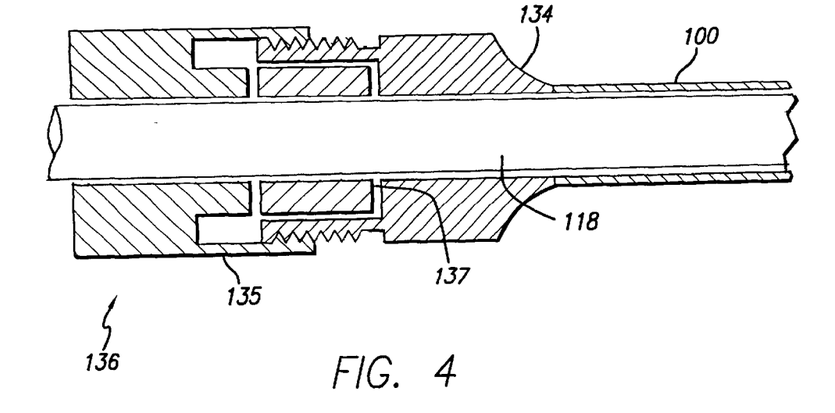
FIG. 4 is a cross-section of the locking mechanism of FIG. 2 shown in an unlocked state.

With reference to FIG. 4, the handle 134 includes a locking mechanism 136 for locking the outer sleeve to the sheath 118 at a selected location. The locking mechanism 136 includes a lock cap 135 and an expandable rubber seal 137, each having a through-hole that allows the sheath 118 to pass through. The seal 137 is positioned between the lock cap 135 and the handle 134. The lock cap 135 engages with the handle 134, such as by a threaded interface or a snap mechanism. As the lock cap 135 is pressed into the seal 137, the seal is constrained by the inside wall of the handle 134 and expands. Expansion of the seal 137 causes the seal through-hole to become smaller and to friction grip the sheath 118. As a result, the locking mechanism 136, handle 135 and outer sleeve 100 are locked in place relative to the sheath 118.

Figure 5A:
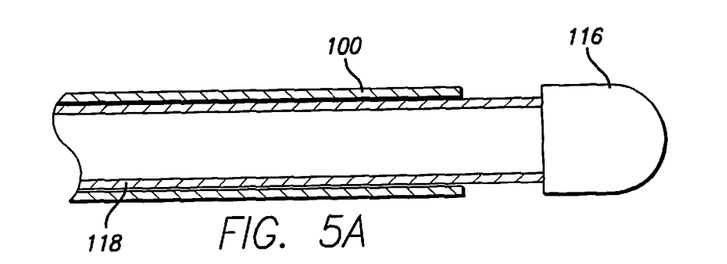
FIGS. 5A and 5B are cross-sections of exemplary mechanisms for retaining the outer sleeve on the catheter sheath, interior components of the sheath have been removed for clarity.
Figure 5B:
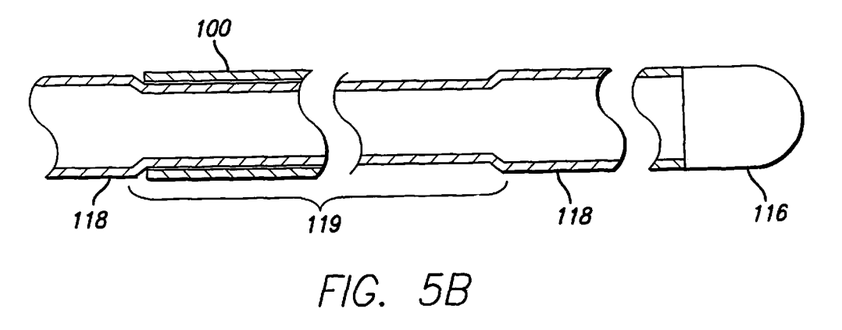

With reference to FIGS. 5A and 5B, in a preferred embodiment the outer sleeve 100 includes a retaining mechanism for ensuring that the distal end of the outer sleeve does not advance past the distal tip of the catheter sheath 118. In one retaining mechanism, as shown is FIG. 5A, the tip electrode 116 is configured such that its outer diameter is greater than the inner diameter of the outer sleeve 100. In an alternate retaining mechanism, as shown in FIG. 5B, the sheath 118 is configured such that the sheath has a narrow section 119 having a diameter less than the inside diameter of the outer sleeve 100. The section of the sheath 118 both distal and proximal the narrow section 119 have a diameter greater than the inside of the outer sleeve 100, as such, movement of the sleeve is limited to the narrow section of the sheath.

Figure 3:
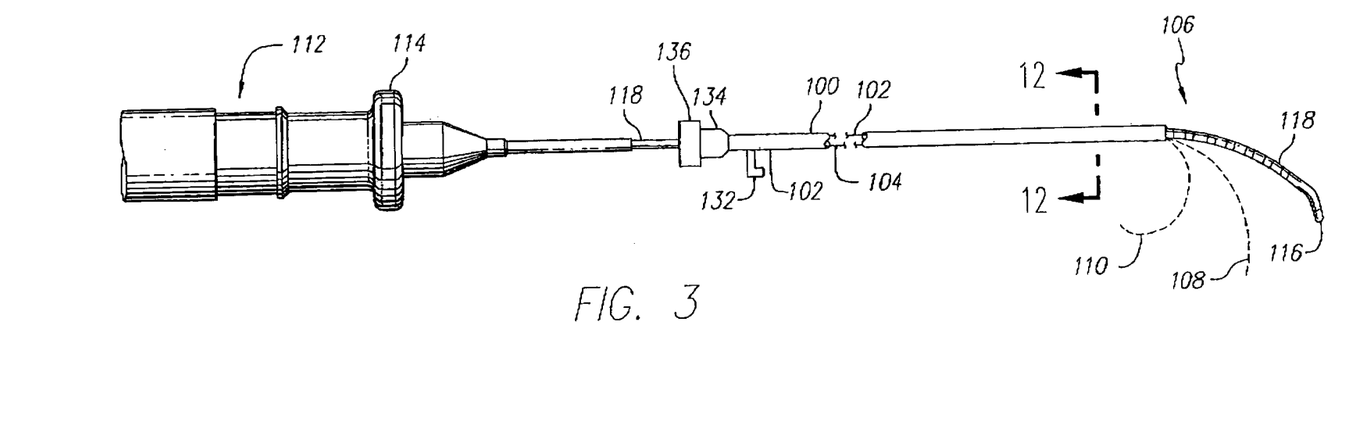
FIG. 3 is a diagram of the catheter system of FIG. 2 with the outer sleeve in an advanced position.

The outer sleeve 100 is formed of a biocompatible material such as Pebax (a Nylon blend) having a stiffness sufficient to change the shape of the preformed distal end, as evident when comparing FIGS. 2 and 3. For example, in one configuration of the catheter the sleeve 100 material has a 63D (Shore D hardness scale) while the distal end of the sheath 106 has a 35 D hardness. In one embodiment, the outer sleeve includes a flush port 132 for flushing out any fluid that enters the space 140 (FIG. 10) between the sheath 118 and the inside surface of the sleeve.

Figure 6:
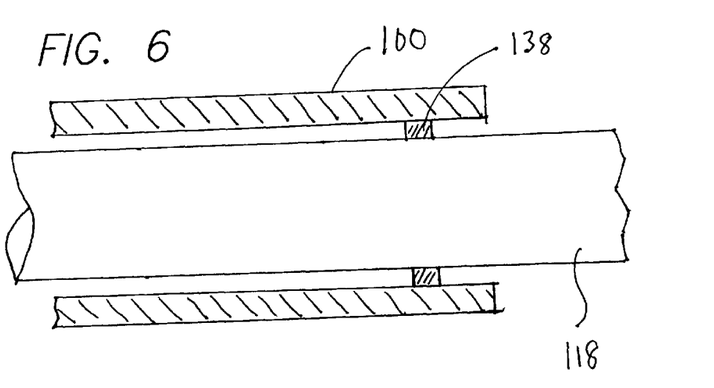
FIG. 6 is a cross-section of the distal end of the outer sleeve depicting a seal positioned between the inner wall of the outer sleeve and the outer wall of the catheter sheath.
Figure 7:
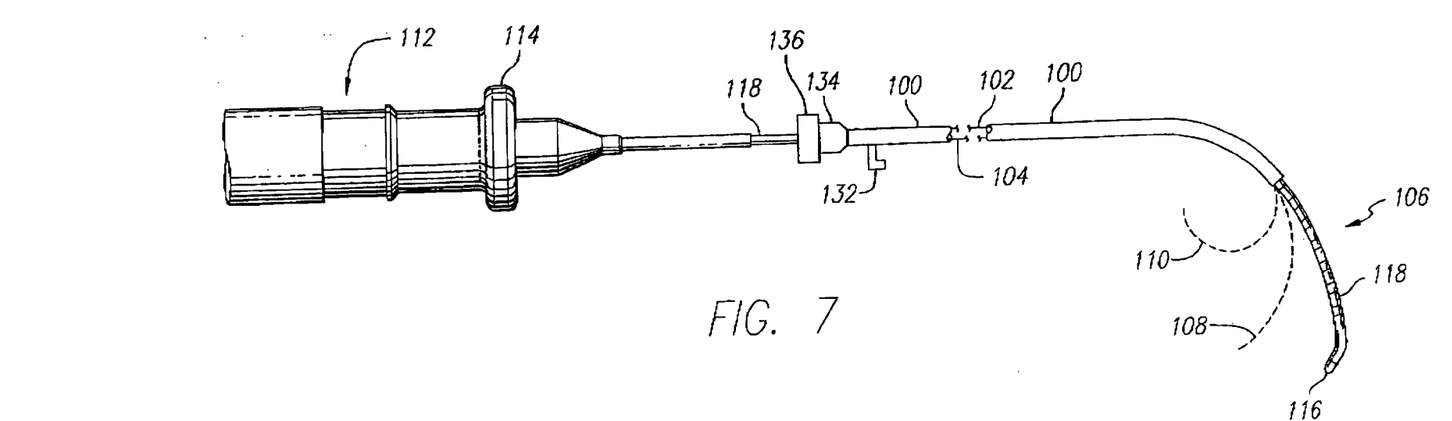
FIG. 7 is a diagram of a catheter system including a handle, steering member, a curved outer sleeve and a catheter sheath having a preformed distal-end region, with the outer sleeve in an advanced position.
Figure 8:
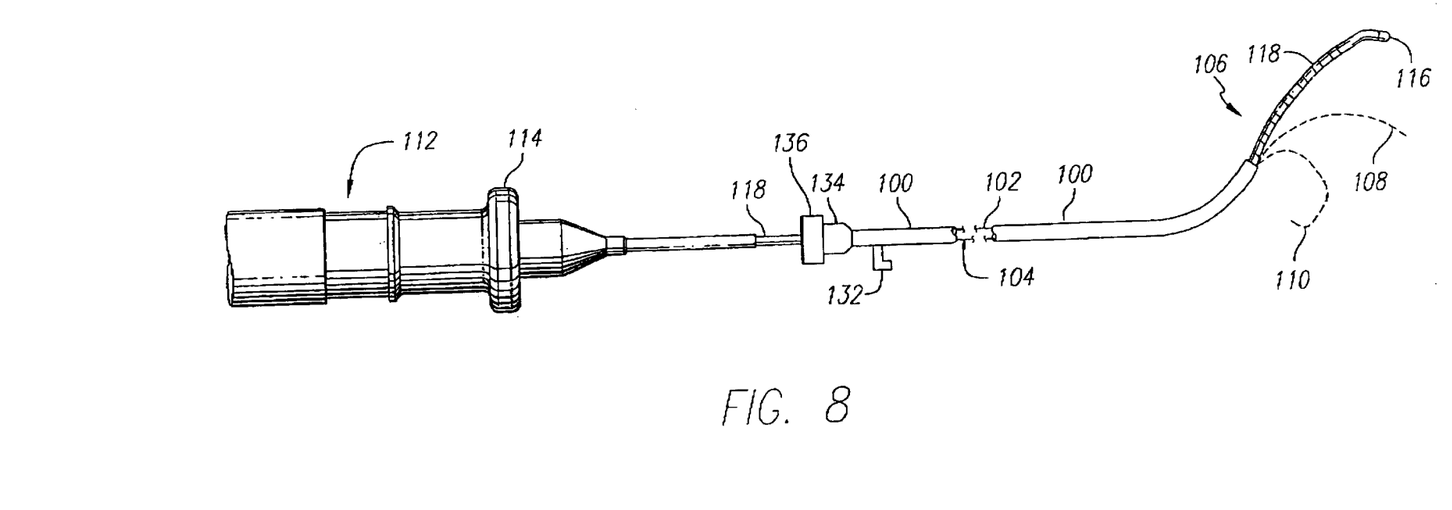
FIG. 8 is a diagram of the catheter system of FIG. 4 with the outer sleeve rotated approximately 180 degrees relative to the outer sleeve in FIG. 4.

With reference to FIG. 6, in another embodiment, the outer sleeve 100 also includes a seal 138. The seal 138 is a soft rubber short-length tubing or o-ring formed of an elastomeric material (silicon, Santoprene, Viton) and is adhered to the inside diameter of the outer sleeve 100 near the distal end. The seal 138 forms a tight seal against the outer surface of the sheath 118 so as to prevent fluid from entering the space 140 (FIG. 10) between the outer sleeve and the sheath. The seal is pliable enough to allow for movement of the outer sleeve 100 relative to the sheath 118 yet rigid enough to function as a seal. As shown in FIGS. 7 and 8, the outer sleeve 102 may also have a preformed distal shape which in this case is a gradual bend of approximately 30 degrees.

The catheter 100 also includes a handle 112 and a steering member 114. A tip component 116 is mounted to the sheath 118 at the very distal tip of the sheath. The stylet 104 (FIG. 9) is located in the distal-end region 106 and preferably runs the entire length of the sheath 118. The stylet 104 is offset from the longitudinal axis of the sheath 118, is attached to the tip component 116 and is anchored to a fixed position within the handle 112. The stylet 104 is formed of an alloy which exhibits a martensitic phase transformation. Such alloys include those which exhibit non-linear superelasticity (typically Ni—Ti with Ni at 49–51.5% atomic) and those which exhibit linear superelasticity (typically Ni—Ti in near equi-atomic composition which has been cold worked). Preferably, the preformed shaped wire 104 is formed of nitinol wire having a diameter in the range of 0.026 to 0.030 mm and a nitinol composition of 49–51.5% Ni. The shape of the distal-end region 106 is created by restraining the nitinol wire in the desired shape and heating the wire to approximately 500° C. for about 10 minutes. The nitinol is then allowed to cool. Upon cooling, the stylet 104 retains the preformed distal shape.

Stress may be applied to the wire to change its shape. For example, as explained below, the stylet 104 may be straightened by the outer sleeve 100 to negotiate its way through a patient's vascular system to the right or left atrium of the heart. Upon removal of the straightening forces, such as when the outer sleeve is retracted, the stylet resumes its preformed shape thereby causing the distal end of the catheter sheath 118 surrounding it to likewise take the same shape. Because of the superelasticity of the nitinol, once the stress is removed the stylet 104 returns to its original shape. This is distinct from other shape-memory materials which are temperature actuated.

Figure 10:
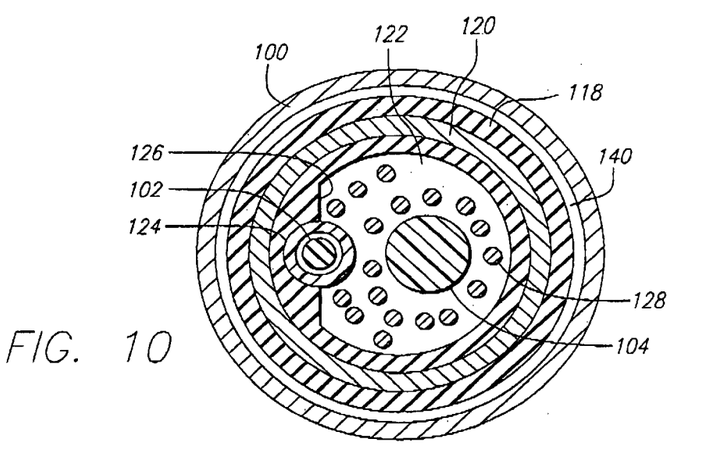
FIG. 10 is a sectional view of the proximal region of the catheter of FIG. 2 taken along the line 10—10 depicting the outer sleeve, catheter sheath with braid, stylet, steering tendon and leads.
Figure 11:
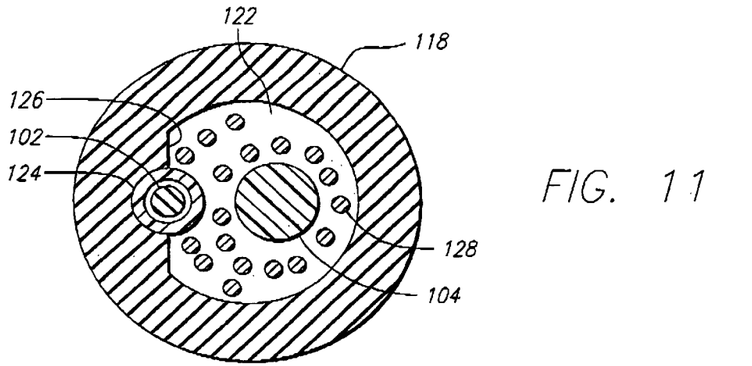
FIG. 11 is a sectional view of the distal-end region of the catheter of FIG. 2 taken along the line 11—11 depicting the catheter sheath, stylet, steering tendon and leads.

Referring now to FIGS. 10 and 11, the stylet 104 is housed inside a composite sheath 118 constructed of different durometers of Pebax and braided stainless steel ribbon in order to tailor the torsinal and bending stiffness in various locations along the length of the catheter. The sheath 118, in turn, is housed inside the outer sleeve 100. The outer sleeve is formed of biocompatible plastic. In the region 130 proximal from the distal-end region 106 (FIG. 2), as shown in the cross section in FIG. 10, the sheath 118 is formed of high durometer Pebax outer jacket having an outside diameter of 2.39 mm (0.094 inches) (7 French) and an inside diameter of 1.58 mm (0.062 inches). Imbedded within the sheath 118 are two layers of braid, 0.001×0.006 stainless steel ribbon 120. The inner lumen 122 has a hollow PTFE tendon sheath 124 bonded to one side 126. The tendon sheath 124 has an outside diameter of approximately 0.457 mm (0.018 inches). The remaining portion of the tendon sheath 124 is exposed in the inner lumen 122.

Figure 9:
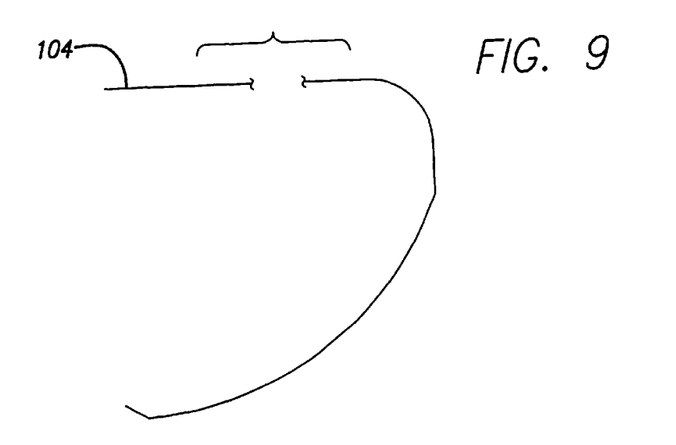
FIG. 9 is a preformed stylet for shaping the distal-end region of the catheter sheaths of FIGS. 2, 3, 7 and 8.

The steering tendon 102 is housed within the tendon sheath 124 and is formed of a stainless steel wire having a diameter of approximately 0.23 mm (0.009 inches). At its distal end, the steering tendon 102 is attached to the tip component 116 at a point parallel to the axis of the tip component. In the alternative, the steering tendon 102 may be anchored at a point proximal the tip component 116. At its proximal end, the tendon 102 is linked to the steering member 114 (FIG. 2) which translates axially along the length of the handle 112. Also housed within the inner lumen 122 are the leads 128. Eighteen are depicted in FIGS. 8 and 9, however, more or fewer may be included depending on the number of electrodes 32 and the configuration of the temperature sensors.

In the distal-end region 106 (FIG. 2), as shown in cross section in FIG. 11, the construction of the sheath 118 is generally the same as that of the proximal region 130 except the outer jacket does not include a stainless steel braid 120. By not including the braid 120, the distal-end region 106 is more flexible than the proximal region 130. Accordingly, the distal-end region 106 is more easily bent for conformance with the biological site. Housed within the sheath 118 and offset from the axis of the sheath is the steering tendon 102.

Figure 13:
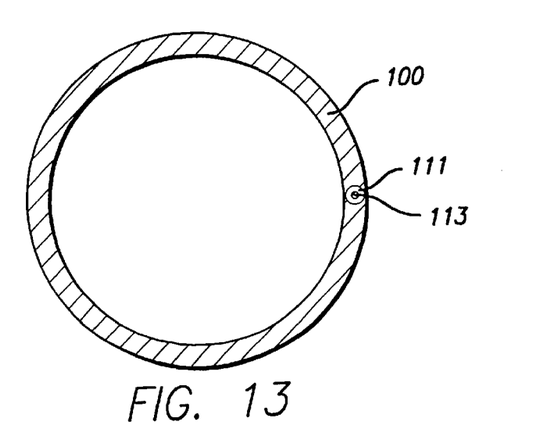
FIG. 13 is a sectional view of the outer sleeve depicting a tendon for deflecting the distal-end region of the outer sleeve.

With reference to FIG. 13, in one embodiment of the catheter, the outer sleeve 100 includes a steering tendon 113 carried by a lumen 111 within the wall of the sleeve. In this configuration of the outer sleeve 100, the distal region may be made of a lower durometer material to enhance sleeve deflection. The tendon 113 is attached to the distal-end region of the sleeve 100, runs the length of the sleeve and exits the proximal end of the sleeve where it is attached to a steering mechanism located on the locking mechanism (not shown). The steering mechanism applies axial tension to the steering tendon to axially displace the tendon and to deflect the distal-end region of the outer sleeve, which alters the radius of curvature (FIGS. 7 and 8) of the distal-end region of the sheath.

Figure 14:
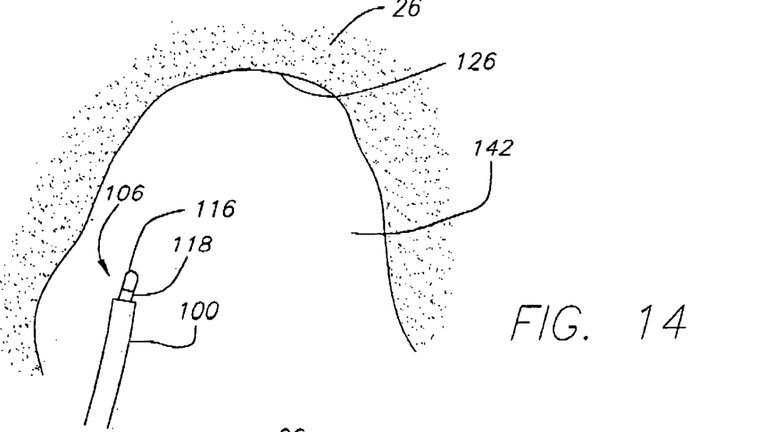
FIG. 14 is a representation of the distal-end region of the catheter of FIG. 3 with the outer sleeve in an advanced position to straighten the catheter sheath for introduction to a biological site.

In operation, the catheter 30 is inserted into a patient's vascular system through an introducer sheath. Prior to being introduced, the outer sleeve 100 is advanced to a position such that substantially all of the distal-end region 106 is within the outer sleeve. With reference to FIG. 14, once introduced into the patient's vascular system, the catheter is guided to the biological cavity 122 e. g., right atrium, containing the tissue to be ablated.

For treatment procedures within the left atrium, the catheter 30 is introduced using a transseptal approach involving a transseptal introducer sheath (not shown). Once the transseptal introducer sheath is positioned between the right and left atria, the catheter 30 is inserted into the introducer sheath. Because of the flexibility of the nitinol stylet 104 and the outer sleeve 100 relative to the stiffness of the transseptal introducer sheath the distal-end region 106 of the sheath 118 and the outer sleeve 100 conform to the shape of the transseptal introducer sheath and follow the tortuous path of the introducer sheath.

Figure 12:
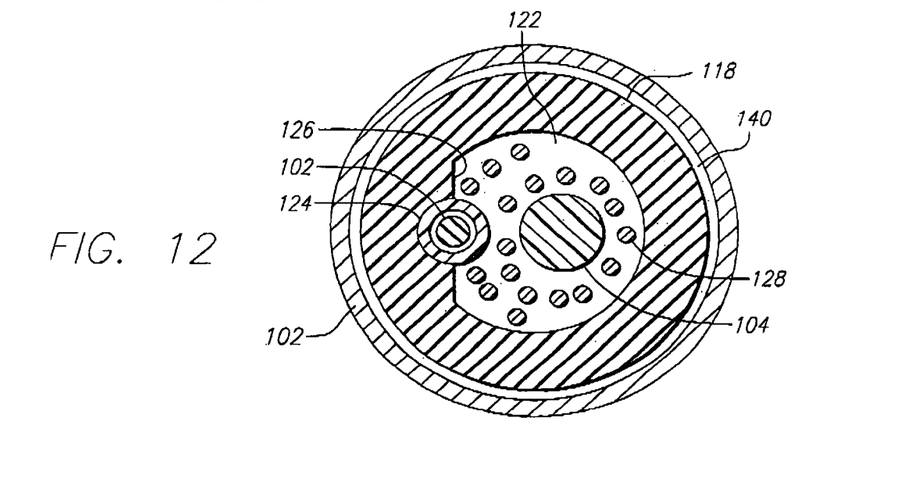
FIG. 12 is a sectional view of the distal-end region of the catheter of FIG. 3 taken along the line 12—12 depicting the outer sleeve, catheter sheath, stylet, steering tendon and leads.

Referring again to FIG. 14, a catheter 30 is shown being introduced to a biological cavity 142. The outer sleeve 100 is in an advanced position so that the distal-end region 106 of the catheter sheath 118 has been placed into a desired linear configuration to more efficiently accomplish the introduction process. In FIG. 14, the sleeve 100 has been advanced and is located over the internal stylet 104 (FIG. 12) and is therefore straightening the stylet and the distal-end region 106 of the catheter. The sleeve 100 is also covering all electrodes when advanced. This may or may not occur, depending on the shape needed for the distal-end region 106 of the catheter 30 during the introduction process.

Figure 15:
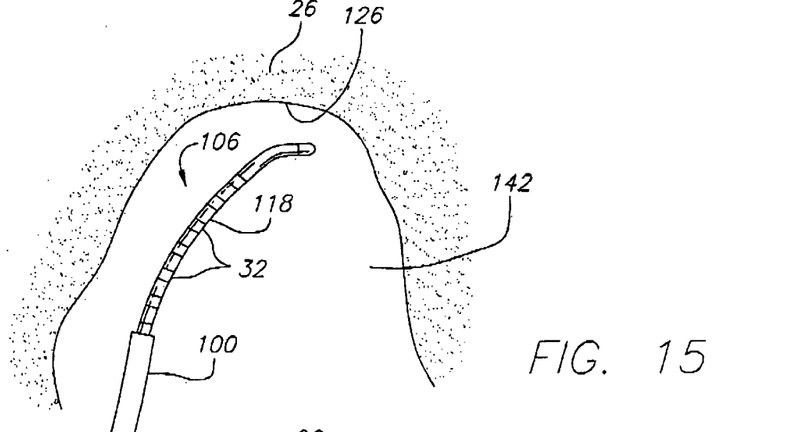
FIG. 15 is a representation of the distal-end region of the catheter of FIG. 11 with the outer sleeve is retracted to allow the catheter sheath to assume its pre-formed shape.

With reference to FIG. 15, once the distal-end region of the catheter enters the biological cavity 142, the catheter sheath 118 is either extended beyond the distal tip of the outer sleeve 100 or the outer sleeve is retracted. In either case, the distal-end region 106 of the sheath 118 is no longer constrained by the outer sleeve 100 and the sheath returns to its original preformed distal shape as dictated by the internal stylet 104.

Once the preformed distal shape is resumed, the distal-end region 106 has a shape more closely following that of the surfaces of the biological cavity 142. However, it may not immediately conform to the shape of the biological site 126 to be ablated as closely as required. Accordingly, the shape of the distal-end region 106 may not allow for some or all of the electrodes 32 to be placed in intimate contact with the tissue 26 to be ablated. If the electrodes 32 are not in contact with the tissue 26, the shape of the distal-end region 106 may be adjusted using the sheath steering tendon, the outer sleeve or a combination of both, such that the electrodes contact the biological tissue 26.

Figure 16:
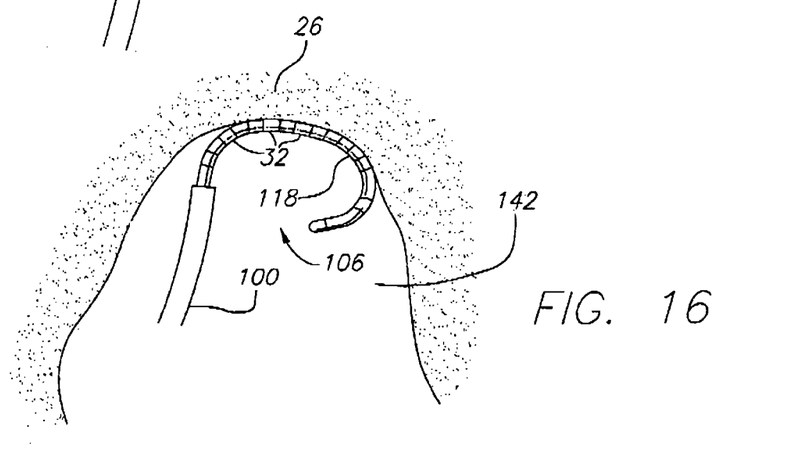
FIG. 16 is a representation of the distal-end region of the catheter of FIG. 12 with the distal-end region of the catheter sheath having a smaller radius of curvature due to movement of the steering tendon and wherein some of the electrodes are in intimate contact with the tissue.

With reference to FIG. 16, using the steering tendon 102, the radius of curvature of the distal-end region 106 may be adjusted. This adjustment is performed by axially displacing the steering member 114 in the proximal direction. In doing so, the steering tendon 102 attached to the tip component 116 experiences tension and causes the sheath 118 to compress on the side in which the steering tendon is positioned and to stretch on the opposite side. This causes the radius of curvature of the distal-end region to decrease. In addition, to further ensure intimate contact between the electrodes 32 and the tissue 26, the handle 112 may be rotated. Because of the attachment of the sheath 118 to the handle 112 and the construction of the catheter, as previously described in relation to FIGS. 10 and 11, this rotational force at the handle causes the catheter to experience a torquing effect along its length, which may aid in positioning the electrodes against the tissue.

The position and shape of the distal-end region 106 may also be adjusted by adjusting the position of the outer sleeve 100. For example, the outer sleeve 100 may be distally advanced relative the distal end of the sheath 118, as shown in FIG. 3. Because the outer sleeve 100 is formed of a material having a stiffness greater than the distal-end region 106, the distal-end region is forced to assume a different shape. Where the outer sleeve 100, itself includes a preformed distal shape, as shown in FIGS. 7 and 8, the position of the distal-end region 106 of the sheath 118 may also be adjusted by rotating the outer sleeve 100 relative to the catheter sheath. In doing so the shape and position of the distal-end region 106 changes.

The distal-end region may also be adjusted by adjusting the position of the outer sleeve 100, locking the outer sleeve in position relative to the sheath 118 using the locking mechanism 136 and rotating the handle 112 to, in turn, simultaneously rotate both the sleeve and the sheath. Also, for outer sleeves 100 having steering capability, the position of the distal-end region 106 extending beyond the distal end of the outer sleeve may be adjusted by applying tension to the outer-sleeve tendon to deflect the outer sleeve along with the distal-end region in a desired direction.

Once the distal-end region 106 is properly positioned and the electrodes 32 are in intimate contact with the tissue, as shown in FIG. 16, RF energy is applied to the electrodes to ablate the tissue. After applying energy to a first portion of tissue 26 located within the selected biological cavity, the distal-end region 106 of the catheter may be repositioned proximal another region of tissue and the curvature of the distal-end region adjusted so that the electrodes 32 contact the tissue. Thus, the catheter provides for ready adjustment of the electrode carrying region 106 such that a plurality of electrodes aligned in a substantially linear array may be placed in intimate contact with tissue 26 to be ablated. Because of the length of the linear electrode array, the device shown in the drawings and described above is particularly suited for performing the Maze procedure in a minimally invasive way.

While certain shapes of the distal end of the catheter are shown in FIGS. 2 and 3, other shapes may be used. The invention is not confined to the shapes shown in these figures. Additionally, the steering tendon 102 and outer sleeve 100 may be used by the operator to steer or assist in advancing the catheter distal end through the blood vessels of the patient to the desired target tissue.

Thus there has been shown and described a new and useful catheter system having a sheath with a preformed distal end and a steering mechanism surrounded by a movable stiffening outer sleeve, the combination of which provide for improved control over the shape of the distal-end region which thereby greatly increases the chances that successful ablation can be obtained in a single procedure.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A catheter comprising:
   a sheath having a distal-end region with a distal tip;
   a tip component mounted to the distal tip of the sheath;
   a wire disposed within the sheath and attached to the tip component, the wire having a distal-end region having a preformed shape with a radius of curvature, the wire formed of a shape-retentive and resilient material such that the wire distal-end region changes shape upon the application of force and upon the removal of force, returns to the preformed shape, the wire disposed in the sheath such that the wire distal-end region is located in the sheath distal-end and causes the sheath to assume the preformed shape;

an outer sleeve having a distal-end region having a distal end, the sleeve surrounding the sheath and positioned relative thereto for movement between a retracted position and any of a plurality of advanced positions during which a portion of the sleeve distal-end region is coincident with a portion of the wire distal-end region, the sleeve formed of a material having a stiffness sufficient to change the shape of the wire distal-end region; and a tendon housed within the sheath and attached to the tip component such that axial displacement of the tendon alters the radius of curvature of the portion of the wire distal-end region extending distal the distal end of the outer sleeve.

2. The catheter of claim 1 wherein the outer sleeve has a fully advanced position during which the sleeve distal end is substantially coincident with the wire distal end.

3. The catheter of claim 1 wherein the outer sleeve has a frilly retracted position during which the sleeve distal-end region is proximal the wire distal-end region.

4. The catheter of claim 1 further comprising an electrode positioned at the distal-end region of the sheath having an outside diameter greater than the inside diameter of the outer sleeve.

5. The catheter of claim 1 wherein the outer sleeve is carried by a section of reduced diameter of the sheath located between a distal sheath section and a proximal sheath section, each of the distal and proximal sheath sections having an outside diameter greater than the inside diameter of the outer sleeve, the section of reduced diameter having an outside diameter less than the inside diameter of the outer sleeve.

6. The catheter of claim 1 wherein the outer sleeve distal-end region comprises a preformed shape with a radius of curvature.

7. The catheter of claim 1 further comprising a tendon housed within a lumen carried by the outer sleeve and attached to the distal-end region of the outer sleeve such that axial displacement of the tendon alters the radius of curvature of the distal-end region of the outer sleeve.

8. The catheter of claim 7 further comprising a steering member positioned at the proximal end of the outer sleeve wherein the outer-sleeve tendon is attached to the steering member for moving the outer-sleeve tendon in an axial direction.

9. The catheter of claim 1 wherein the sheath has an axis and the outer sleeve is positioned for rotational movement about the axis of the sheath.

10. The catheter of claim 1 further comprising a handle having the proximal end of the sheath and the wire connected thereto such that rotation of the handle results in rotation of the sheath and wire.

11. The catheter of claim 1 further comprising a locking mechanism for locking the outer sleeve in a position relative to the sheath.

12. The catheter of claim 11 further comprising a handle having the proximal end of the sheath and the wire connected thereto such that when the outer sleeve is locked to the sheath, movement of the handle results in movement of the sheath, wire and outer sleeve.

13. The catheter of claim 1 further comprising a seal between the outer-sleeve inner surface and the sheath outer surface.

14. The catheter of claim 1 wherein the sheath tendon is disposed in the sheath such that pulling the sheath tendon in the proximal direction decreases the radius of curvature of the wire distal-end region distal the distal end of the sleeve and subsequent movement of the sheath tendon in the distal direction allows an increase in the radius of curvature of the wire distal-end region distal the distal end of the sleeve.

15. The catheter of claim 1 further comprising a steering member positioned at the proximal end of the sheath wherein the sheath tendon is attached to the steering member for moving the sheath tendon in an axial direction.

16. An ablation catheter for use in applying energy to heart tissue, said system comprising:

a catheter sheath having a distal-end region with a distal tip;

a tip component mounted to the distal tip of the catheter sheath;

at least one electrode located at the sheath distal-end region;

a wire disposed within the sheath and attached to the tip component, the wire having a distal-end region with a preformed shape with a radius of curvature, the wire formed of a shape-retentive and resilient material such that the wire distal-end region changes shape upon the application of force and upon the removal of the force, returns to the preformed shape, the wire disposed in the catheter sheath such that the wire distal-end region is located in the distal-end region of the sheath and causes the sheath to assume the preformed shape;

an outer sleeve having a distal-end region having a distal end, the sleeve surrounding the sheath and positioned relative thereto for movement between a retracted position and any of a plurality of advanced positions during which a portion of the sleeve distal-end region is coincident with a portion of the wire distal-end region, the sleeve formed of a material having a stiffness sufficient to change the shape of the wire distal-end region;

a tendon housed within the sheath and attached to the tip component such that axial displacement of the tendon changes the radius of curvature of the portion of the wire distal-end region extending distal the distal end of the outer sleeve;

a locking mechanism for locking the outer sleeve in a position relative to the sheath; and a handle attached to the proximal end of the catheter sheath and the wire such that movement of the handle causes movement of the catheter sheath, the wire and the outer sleeve.

17. The ablation catheter of claim 16 further comprising a steering member on the handle and connected to the tendon such that movement of the steering member causes axial movement of the tendon to control changes in the radius of curvature of the wire distal-end region.

18. A method for applying energy to biological tissue within a biological chamber of a patient using a catheter having a sheath having a distal end-region with a distal tip, the distal-end region of the sheath carrying a plurality of electrodes and having a predetermined shape; a wire disposed within the sheath and attached to the tip component, the wire having a distal-end region having a preformed shape with a radius of curvature, the wire formed of a shape-retentive and resilient material such that the wire distal-end region changes shape upon the application of force and upon the removal of force, returns to the preformed shape, the wire disposed in the sheath such that the wire distal-end region is located in the sheath distal-end and causes the sheath to assume the preformed shape; an outer sleeve having a distal-end region having a distal end, the sleeve surrounding the sheath and positioned relative thereto for movement between a retracted position and any of a plurality of advanced positions during which a portion of the sleeve distal-end region is coincident with a portion of the wire distal-end region, the sleeve formed of a material having a stiffness sufficient to change the shape of the wire distal-end region; and a tendon housed within the sheath and attached to the tip component such that axial displacement of the tendon changes the radius of curvature of the portion of the wire distal-end region extending distal the distal end of the outer sleeve, said method comprising:

placing the outer sleeve in an advanced position such that a portion of the distal end of the sheath is positioned within the outer sleeve;

inserting the catheter into the vasculature of the patient;

advancing the catheter into the biological chamber in which the selected tissue is located;

retracting the outer sleeve such that a portion of the distal-end region of the sheath is positioned outside of the outer sleeve thereby permitting the wire distal-end region to assume the preformed shape;

advancing the distal-end region of the catheter sheath to a position proximal the selected biological tissue; and     adjusting the radius of curvature of the distal-end region of the wire to thereby affect adjustment in the distal-end region of the sheath such that a plurality of the electrodes contact the selected biological tissue.

19. The method of claim 18 wherein advancing the distal-end region of the catheter sheath to a position proximal the selected heart tissue comprises the step of securing the outer sleeve to the sheath and axially displacing the catheter toward the selected biological tissue.

20. The method of claim 18 wherein advancing the distal-end region of the catheter sheath to a position proximal the selected heart tissue comprises the step of maintaining the position of the outer sleeve while axially displacing the catheter sheath toward the selected biological tissue.

21. The method of claim 18 wherein adjusting the radius of curvature of the distal-end region of the catheter comprises the step of displacing the tendon to deflect the wire distal-end region and thereby alter the curvature of the wire distal-end region.

\* \* \* \* \*